United States Patent [19]

Jäger et al.

[11] 4,136,039
[45] Jan. 23, 1979

[54] BORIC ACID/AMINE REACTION PRODUCTS, THEIR MANUFACTURE AND USE

[75] Inventors: Horst Jäger, Bettingen; Hans Wegmüller, Riehen, both of Switzerland

[73] Assignee: Ciba-Geigy Corporation, Ardsley, N.Y.

[21] Appl. No.: 810,837

[22] Filed: Jun. 28, 1977

[30] Foreign Application Priority Data

Jul. 8, 1976 [LU] Luxembourg .............................. 75333

[51] Int. Cl.² .............................................. D06M 13/34
[52] U.S. Cl. ....................................... 252/8.8; 252/8.9; 252/62.2; 260/462 R
[58] Field of Search ........................ 252/8.8, 8.9, 62.2; 260/462 R

[56] References Cited

U.S. PATENT DOCUMENTS

| 2,052,192 | 8/1936 | Piggott | 260/462 R |
|---|---|---|---|
| 2,084,046 | 6/1937 | Owen | 260/462 R |
| 2,878,144 | 3/1959 | Conbere et al. | 260/462 R |
| 3,639,234 | 2/1972 | Wixon et al. | 260/462 R |
| 3,660,459 | 5/1972 | Hughes | 260/462 R |
| 3,804,875 | 4/1974 | Ludwig et al. | 260/462 |

*Primary Examiner*—William E. Schulz
*Attorney, Agent, or Firm*—Edward McC. Roberts; Prabodh I. Almaula

[57] ABSTRACT

The present invention relates to boric acid/amine reaction products of (a) boric acid and (b) an amine of the formula

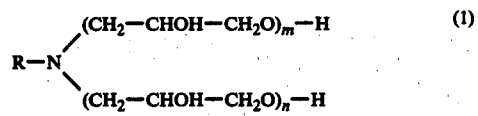

in which R denotes optionally substituted alkyl, alkenyl, aryl or cycloalkyl or an optionally substituted heterocyclic radical and m and n are each a number from 1 to 6. These products are used as auxiliaries in the textile, leather, detergent and cosmetics industry.

12 Claims, No Drawings

BORIC ACID/AMINE REACTION PRODUCTS, THEIR MANUFACTURE AND USE

The present invention relates to boric acid/amine reaction products of (a) boric acid and (b) an amine of the formula

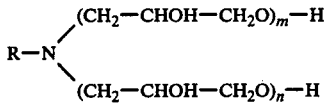 (1)

in which R denotes optionally substituted alkyl, alkenyl, aryl, or cycloalkyl or an optionally substituted heterocyclic radical and m and n are each a number from 1 to 6.

The boric acid can be both the preferred orthoboric acid, and metaboric acid or tetraboric acid, or the corresponding salts, such as alkali metal salts. Depending on the nature of the boric acid, more or less water is liberated during the reaction with the amine of the formula (1).

The tertiary amine of the formula (1) is the reaction product of a primary amine and 2 to 12 mols of glycidol, that is to say, in the simplest case, a N-substituted bis-2,3-dihydroxypropylamine. The amines can be manufactured in the melt or in an inert, organic solvent, such as petroleum ether, cyclohexane, benzene, toluene or xylene. As a rule, the reaction temperature is 50 to 120° C, preferably about 50 to 100° C.

Preferred amines correspond to the formula

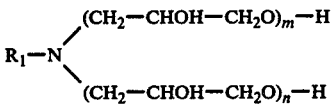 (2)

in which $R_1$ denotes alkyl or alkenyl with at most 22 carbon atoms, optionally substituted by hydroxyl, alkoxy with 1 to 12 carbon atoms, phenoxy, phenyl or halogen; or a cycloalkyl radical with 5 or 6 carbon atoms, phenyl radical, naphthyl radical or heterocyclic radical with 5 or 6 ring members and 1 or 2 heteroatoms, optionally substituted by alkyl with 1 to 12 carbon atoms, alkenyl with 2 to 12 carbon atoms, alkoxy with 1 to 12, in particular 1 to 8, carbon atoms, phenoxy, hydroxyl or halogen, and m and n are each a number from 1 to 6.

Amines of the formula

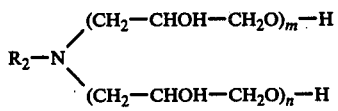 (3)

in which $R_2$ denotes alkyl with 1 to 22 carbon atoms, phenyl, alkylphenyl with 1 to 22 carbon atoms in the alkyl radical, cyclohexyl or a heterocyclic radical with 6 ring members and 1 or 2 nitrogen or oxygen atoms as the heteroatom and m and n each denote a number from 1 to 6, are of particular interest as component (b).

Amines which are well-suited preferably correspond to the formula

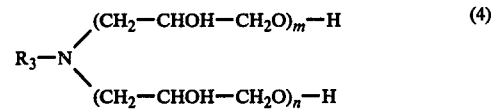 (4)

in which $R_3$ denotes alkyl with 1 to 22, preferably 4 to 22 and in particular 12 to 22, carbon atoms.

The amines of the formulae (1) to (4) can be both amines with a uniform number of dihydroxypropyl radicals and amines in which the two chains contain a different number of dihydroxypropyl radicals. Furthermore, the amines can also be present as mixtures with different chain lengths, so that m and n are average values and can thus also represent fractions. Preferably, however, m and n represent integers and are identical. m and n are peferably each 1 or 2, above all each 1.

The boric acid/amine reaction products are preferably obtained by reacting 1 mol of boric acid and 1 mol of amine.

Preferred boric acid/amine reaction products probably correspond to the formula (5a) or contain structural elements of the formula (5b)

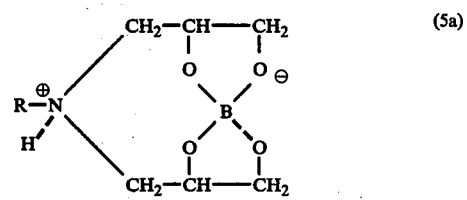 (5a)

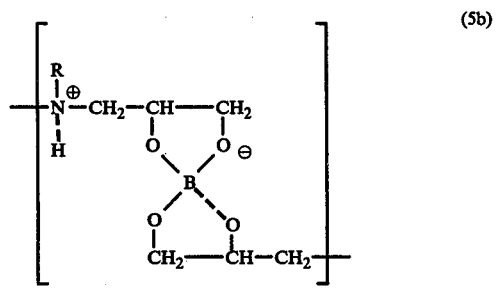 (5b)

in which R has the meaning indicated.

Amongst these reaction products, those of the formula (6a) or (6b)

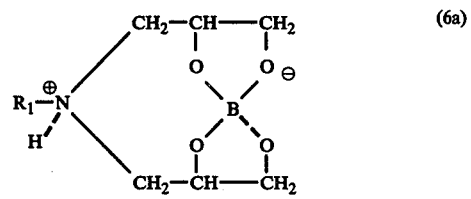 (6a)

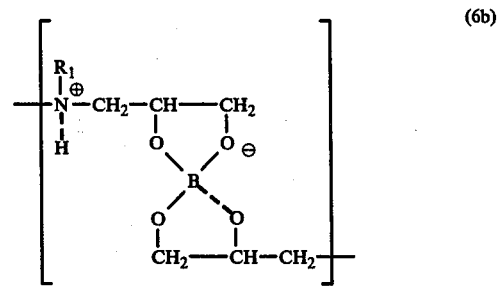 (6b)

in which $R_1$ has the meaning indicated, claim particular interest.

Reaction products which are well-suited correspond to the formula

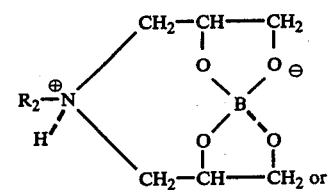
(7a)

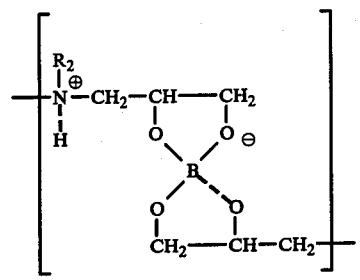
(7b)

and, above all, to the formula

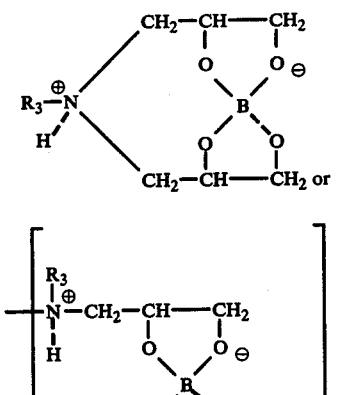
(8a)

(8b)

in which $R_2$ and $R_3$ have the meaning indicated.

Other preferred boric acid/amine reaction products probably contain structural elements of the formula

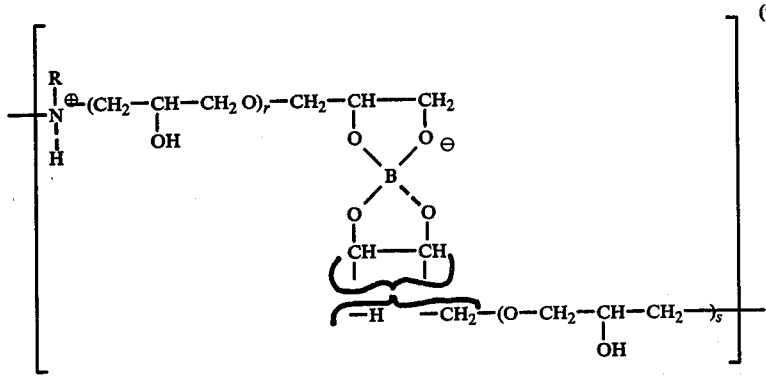
(9)

in which R has the meaning indicated and r and s each represent an integer from 1 to 6, and wherein the two free terminal valencies saturate one another so that a monomeric product is present or, preferably, are bonded to other structural elements of the formula (9) so that polymeric products are present. As a rule, polymeric products are linear. In the general sense, these comments also apply to the formulae (5b), (6b), (7b) and (8b). In the case of polymeric products, the number of structural elements of the formulae (5b), (6b), (7b), (8b) and (9) is 2 to 1,000. For preferred products, R in the formula (9) can also be replaced by $R_1$, $R_2$ or $R_3$.

In the definitions of the R radicals, alkyl represents both substituted and unsubstituted, straight-chain or branched alkyl with chain lengths of, for example, 1 to 22 carbon atoms. Thus radicals such as methyl, ethyl, n-butyl, tert.-butyl, sec.-butyl, iso-butyl, n-hexyl, iso-octyl and n-nonyl, but above all lauryl, cetyl, stearyl and behenyl are suitable, it being possible for these radicals to be further substituted, for example by hydroxyl or by alkoxy with, for example, 1 to 8 carbon atoms, it being possible here for these to be alkoxy radicals which are analogous to the alkyl radicals, or by aroxy radicals, such as phenoxy or naphthoxy, by aryl radicals, such as phenyl or naphthyl, or by halogen, such as fluorine, chlorine, bromine or iodine. The corresponding alkenyl radicals, which contain, for example, 2 to 24 carbon atoms, can also contain the same substitutents. Examples of alkenyl are allyl, butenyl, hexenyl, decenyl, oleyl or erucyl.

Possible aryl radicals in the definition of R are, above all, optionally substituted phenyl or naphtyl, the same substituents as indicated for alkyl being possible. In addition, the aromatic radicals can also be further substituted by alkyl or alkenyl themselves, the same radicals as indicated above being again possible.

The cycloalkyl radical can be, for example, the cyclopentyl or, in particular, the cyclohexyl radical. These radicals are preferably unsubstituted or are further substituted in the same manner as the aromatic radicals.

Heterocyclic radicals preferably contain 5 or 6 ring members and sulphur, oxygen or nitrogen as heteroatoms. As a rule, these radicals contain two, or preferably, one heteroatom. Examples which may be mentioned are the radicals os isoxazole, N-methylpiperidine, pyridine or morpholine. These radicals can also be further substituted in the same manner as the aromatic radicals.

Instead of amines of the formulae (1) to (4), their quaternization products or the corresponding amine oxides can also be used as component (b). On the other hand, it is also possible to quaternize the boric acid/amine reaction products according to the invention themselves or to convert them into the amine oxides.

These modifications can be carried out according to customary methods. Quaternizing agents which can be used are the customary agents, such as, for example, methyl chloride or dimethyl sulphate, and an oxidising agent which can be used is, preferably, hydrogen peroxide.

In the manufacture of the boric acid/amine reaction products, the procedure is such that (a) boric acid is reacted with (b) an amine of the formula (1) or one of the formulae (2) to (4) in the presence of an inert, organic solvent and optionally in the presence of a catalyst.

As a rule the reaction is carried out at temperatures from 10 to 150° C, preferably from 80 to 150° C and in particular below 100° C, for example 80 to 95° C. The water formed during the reaction by the esterification of boric acid is appropriately continuously distilled off azeotropicallly. Above all, aromatic hydrocarbons, such as xylene, toluene or, above all, benzene, have proved to be suitable inert, organic solvents.

The molar radio between the two components can vary, but about 1 mol of boric acid is preferably reacted with about 1 mol of amine.

In addition, catalysts can be employed during the reaction; these catalysts are, for example: tertiary amines, their salts or quaternary ammonium compounds, for example benzyldimethylamine, benzyltrimethylammonium hydroxide, 1-methyl-imidazole or 2-ethyl-4-methyl-imidazole, or alkali metal alcoholates, such as, for example, sodium methylate.

The boric acid/amine reaction products are amphoteric compounds with properties which allow them to be employed in many fields, for example as auxiliaries in the textile, leather, paper, detergent or cosmetics industry.

Depending on the meaning of $R$, $R_1$, $R_2$ or $R_3$, the boric acid/amine reaction products are suitable for use as antistatic agents or anti-soiling agents in the treatment of textiles. They can be employed as brightening agents in the processing of synthetic fibres, for example polyacrylonitrile fibres. In detergents, they can be employed as anti-soil redeposition agents.

As a result of their good, surface-active properties, the products are, of course, also suitable for use as emulsifiers or dispersing agents with protective colloid properties. As a rule, the reaction products cause a relatively sharp increase in the viscosity of the formulations to which they are added, and in most cases are distinguished by a good insensitivity towards the addition of electrolytes.

The many good surface-active properties of the reaction products according to the invention also enable them to be employed in cosmetics, in particular in agents for hair care, such as hair shampoos, hair setting lotions, hair conditioners and hair fixatives, and furthermore also in skin creams or perfume vehicles.

The products according to the invention can improve the ease of combing the hair when wet and dry, can impart an antielectrostatic finish to the hair and can have a slight fixative effect on the hairstyle. Furthermore, these products also have antimicrobial properties.

In addition, the products according to the invention are also suitable for improving and stabilising the aspect of detergents containing anionic optical brighteners.

In the examples which follow, percentages and parts relate to the weight.

EXAMPLE 1 a. 1,000 ml of toluene are initially introduced into a 2 l stirred vessel with a condenser with a vent, thermometer, dropping funnel and heating, and 269 g of stearylamine are dissolved in this. Thereafter, the temperature is adjusted to 50° C. 164.45 g of glycidol having an epoxide content of 90% (which corresponds to 148 g of 100% pure material) are added dropwise in the course of 45 minutes. During this addition, the internal temperature rises to 62° C, at an external temperature of 50 – 52° C. After the dropwise addition has ended, the external temperature is increased to 60° C, whereupon the internal temperature rises to 80° C in the course of 20 minutes and then, after about 20 minutes, falls again to 70° C. The mixture is subsequently boiled under reflux for 6 hours to complete the reaction and then cooled. A light yellow, soft waxy product is obtained in virtually quantitative yield.

b. 62 g of orthoboric acid are introduced into the solution of bis-2,3-dihydroxypropyl-stearylamine in toluene. The solution is heated to the reflux temperature, whilst stirring rapidly, and 54 g of water are removed by azeotropic distillation. The residue is freed from toluene in vacuo. A pale yellow, brittle, resinous product is obtained which is water-soluble and probably corresponds to the formula

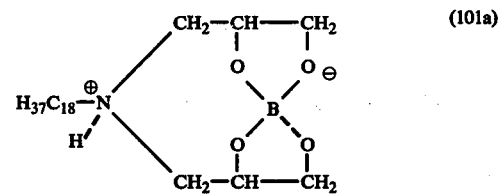
(101a)

or contains structural elements of the formula

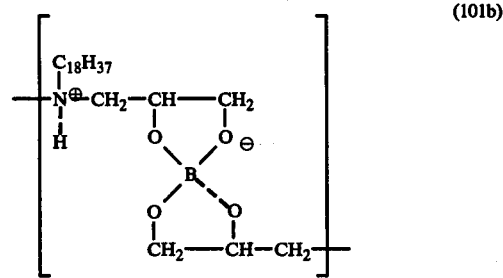
(101b)

Yield: 441 g = 100% of theory.
Analysis: $C_{24}H_{48}BNO_4$
Calculated C 68.20%; H 11.18%; O 15.12%, N 3.31%; B 2.55%; Found: C 67.1%; H 11.3%; N 3.3%; B 2.3%.

EXAMPLES 2 - 5

The following are manufactured in a manner analogous to that described in Example 1:
2. From n-butylamine: $C_{10}H_{20}BNO_4$; yield: 98%.
Calculated: C 52.43%; H 8.79%; O 27.93%; N 6.11%; B 4.72%; Found: C 51.6%; H 8.9%; N 6.1%; B 4.5%;
3. From laurylamine: $C_{18}H_{36}BNO_4$; yield: 95%.
Calculated: C 63.34%; H 10.63%; O 18.75%; N 4.10%; B 3.17%; Found: C 63.0%; H 10.7%; N 4.0%; B 2.9%;
4. From cetylamine: $C_{22}H_{44}BNO_4$; yield: 97%.

Calculated: C 66.49%; H 11.16%; O 16.10%; N 3.52%; B 2.72%; Found: C 66.6%; H 10.9%; N 3.5%; B 2.6%;

5. From a $C_{20}$-$C_{22}$-alkylamine: $C_{26-28}H_{56}BNO_4$: yield: 98.6%.

Calculated for $C_{28}$: C 69.80%; H 11.70%; O 13.30%; N 2.91%; B 2.25%; Found: C 67.9%; H 11.4%; N 2.9%; B 2.2%;

Whilst the product according to Example 2 is a water-soluble syrup, the products according to Examples 3 to 5 are brittle and water-soluble.

EXAMPLE 6

Example 1 is repeated, but 1 g of benzyltrimethylammonium hydroxide is added to stage (a) as a catalyst. The reaction starts immediately at 60° C. The reaction mixture is kept at 90° C for 3 hours. The end point of the reaction is determined the epoxide titre. After 3 hours, the epoxide titre is 0.

Stage (b) is carried out unchanged, as described in Example 1. Yield: 98% of theory.

The formulation is identical to the product from Example 1 and corresponds to the probable formula (101a) or (101b).

EXAMPLE 7 a. 241 g of cetylamine (1 mol) are melted at 60° C and 148 g of glycidol (2 mols) are added dropwise in the course of 120 minutes. The temperature is kept at 90° C by cooling. The mixture is then reacted for a further 3 hours at 105° C.

b. The waxy product is dissolved hot in 1,000 ml of toluene and reacted with 62 g of boric acid as described in Example 1. The isolated formulation is virtually identical in yield and analysis to the formulation of Example 3.

EXAMPLE 8

Cetylamine is reacted as described in Example 7, but 1.0 g of benzyltrimethylammonium hydroxide is added as a catalyst. The reaction of stage (a) starts immediately, is kept at 90° C by cooling and has ended within one hour.

The formulation isolated from stage (b) is identical to the formulation from Example 7.

EXAMPLE 9

As indicated in Example 1, stage (a), 1 mol of cetylamine is subjected to a condensation reaction once with 5 mols of glycidol and once with 7 mols of glycidol and the products are then reacted with 1 mol of boric acid as described in Example 1, stage (b). Water-soluble, resinous, brittle products are obtained which contain 5 or, respectively, 7 mols of glycidol and, in each case, 1 mol of boric acid co-condensed.

5 mols of glycidol
$C_{31}H_{62}BNO_{10} \cdot H_2O$; yield: 89%.
Calculated: C 58.4%; H 10.01%; B 1.7%; N 2.2%; O 27.6%;
Found: C 58.4%; H 9.6%; B 2.5%; N 2.1%; O 27.4%;

7 mols of glycidol
$C_{37}H_{74}BNO_{15} \cdot H_2O$; yield: 93%.
Calculated: C 55.5%; H 9.5%; B 1.4%; N 1.7%; O 31.9%; Found: C 55.6%; H 9.62%; B 1.6%; N 1.7%; O 31.5%;

EXAMPLES 10 to 13

The following are manufactured in a manner analogous to that described in Example 1:

10. From 1 mol of 3-amino-5-methylisoxazole, 2 mols of glycidol and 1 mol of orthoboric acid Yield: 93% of theory
$C_{10}H_{15}N_2O_5B$:
Calculated: C 47.27%; H 5.95%; N 11.03%; O 31.49%; B 4.26%; Found: C 48.2%; H 6.4%; N 8.2%; O 33.2%; B 4.0%;

The compound still contains a third of a glycidol radical per mol.

11. From 1 mol of p-toluidine, 3 mols of glycidol and 1 mol of orthoboric acid
Yield: 96% of theory
$C_{16}H_{25}NO_6B$
Calculated: C 56.82%; H 7.45%; N 4.14%; O 28.28%; B 3.20%; Found: C 57.02%; H 7.4%; N 4.52%; O 28.32%; B 2.82%;

12. From 1 mol of cyclohexylamine, 2 mols of glycidol and 1 mol of orthoboric acid
Yield: 82% of theory
$C_{12}H_{21}NO_4B$
Calculated: C 56.72%; H 8.33%; N 5.51%; O 25.10%; B 4.25%; Found: C 55.1%; H 9.32%; N 4.5%; B 4.2%;

The analysis is only inaccurate since the product still contains included solvent.

13. From 1 mol of 2-amino-4-methyl-pyridine, 2 mols of glycidol and 1 mol of orthoboric acid
Yield: 60% of theory
$C_{15}H_{22}N_2O_6B$
Calculated: C 53.43%; H 6.65%; N 8.37%; O28.42%; B 3.21%; Found: C 51.0%; H 6.7%; N 8.5%; O 30.4%; B 3.4%;

EXAMPLE 14

1 mol of a $C_{20-22}$-alkylamine is reacted with 8 mols of glycidol and then with 1 mol of orthoboric acid in a manner analogous to that indicated in Example 1. A pale yellow glassy soft product is obtained in a yield of 95%.

The elementary analysis for the empirical formula $C_{45}H_{90}NO_{16}B$ gives:
Calcuated: C 59.26%; H 9.94%; N 1.53%; O28.07%; B 1.18%; Found: C 59.01%; H 10.05%; N 1.45%; O28.39%; B 1.10%:

EXAMPLE 15

A sample of a synthetic polyamide woven fabric dyed with an acid dyestuff, together with an undyed knitted fabric, is boiled for 60 minutes in a bath which contains a boric acid/amine reaction product, dried and evaluated with respect to the migration improvement. The evaluation scale runs from 0 to 100%. 0% means that the undyed sample is not stained and 50% means that a complete balancing-out between the dyed and undyed accompanying fabric has taken place.

| Dye bath | Concentration Evaluation | Concentration Evaluation |
|---|---|---|
| Dyestuff | 0.2% | 0.2% |
| Boric acid/amine reaction product according to Example 1 or 4 | 2% | 4% |
| pH 4.5 | 40% | 45% |
| pH 5.0 | 40% | 45% |
| pH 6.0 | 40% | 45% |
| Dyeing without a boric | | |

-continued

| Dye bath | Concentration Evaluation | Concentration Evaluation |
|---|---|---|
| acid/amine reaction product | | |
| pH 4.5 | | 5% |
| pH 5.0 | | 15% |
| pH 6.0 | | 35% |

EXAMPLE 16

The boric acid/amine reaction products in a low concentration very greatly reduce the surface tension of water.

| Product according to Example | Concentration % | dynes/cm 20° C | |
|---|---|---|---|
| Example 3 | 0.005 | 48.2 | Amphoteric boric |
| | 0.01 | 34.8 | acid complexes in |
| | 0.05 | 33.5 | small amounts |
| | 0.1 | 33.4 | reduce the surface |
| | | | tension of water |
| Example 4 | 0.001 | 44.0 | almost as greatly |
| | 0.005 | 35.3 | as the known per- |
| | 0.01 | 34.6 | fluorocarbon |
| | 0.05 | 33.2 | compounds. They |
| | 0.1 | 33.1 | are thus very suit- |
| | | | able for use as |
| | | | dispersing agents. |
| Example 1 | 0.001 | 47.7 | |
| | 0.005 | 41.8 | |
| | 0.01 | 39.5 | |
| | 0.05 | 36.0 | |
| | 0.1 | 35.4 | |
| Comparison: | | | |
| Water | | 71.7 | |
| Ethanol | | 47.4 | |

EXAMPLE 17

Emulsions A to I according to the table which follows are prepared.

| Components of the emulsion in parts | Emulsion | | | | | | | | |
|---|---|---|---|---|---|---|---|---|---|
| | A | B | C | D | E | F | G | H | I |
| Reaction product according to Example 4, 7 or 9 | 0.1 | 0.5 | 0.5 | 0.5 | 0.5 | 0.5 | 0.5 | 0.5 | 0.5 |
| Water (distilled) | 24.9 | 24.5 | 22.0 | 20.5 | 21 | 19.5 | 23.5 | 23.5 | 23.5 |
| Light paraffin oil | 75 | 75 | 75 | 75 | 75 | 75 | 75 | 75 | 75 |
| 1N HCl | — | — | 2.5 | — | 2.5 | — | — | — | — |
| 1N NaOH | — | — | — | 4.0 | — | 4.0 | — | — | — |
| NaCl | — | — | — | — | 1.0 | 1.0 | — | — | — |
| NaH$_2$PO$_4$ | — | — | — | — | — | — | 1.0 | — | — |
| Na$_2$HPO$_4$ | — | — | — | — | — | — | — | — | 1.0 |
| pH of the emulsion | 7.0 | 7.0 | 2.0 | 11.0 | 2.0 | 11.0 | 5.0 | 7.0 | 11.0 |

All the emulsions are stirred vigorously for 120 seconds and all are stable even after prolonged storage.

EXAMPLE 18

An emulsion which can be diluted as desired with water is prepared, whilst circulating, from the components which follow by means of a high pressure emulsifying pump under a pressure of 400 bars and at 50° C in the course of 60 minutes:

52.5 g of dimethylpolysiloxane,
210.0 g of methylhydrogenopolysiloxane,
10.5 g of perchloroethylene,
35.0 of toluene,
6.1 g of hydrochloric acid (37% strength),
15.0 g of the reaction product according to Example 4, 7 or 9 and
545.0 g of water.

After providing textile surfaces with a water-repellent finish with this emulsion, the following water absorptions (Bundesmann test) are determined:
3% polyamide
7% polyester/cotton
14% cotton

EXAMPLE 19

The reaction products according to Examples 1, 3, 5 and 8 are dissolved in water to the extent of 1% and 2%. Polyacrylonitrile flocks finished with these solutions exhibit good antielectrostatic properties. The flocks do not stick together, the suppleness and slip are increased and the spinnability of the flock is thus facilitated.

EXAMPLE 20

A 1% strength aqueous solution of the reaction product according to Example 1 is tested as a hair setting lotion on a strand of hair, the result being that the ease of combing when wet, the ease of combing when dry and the ease of washing out are very good, the shine and the hold of the set are good and no electrical charging occurs.

EXAMPLE 21

The reaction product according to Example 14 is employed in concentrations of 0.1%, 0.2%, 0.5%, 1% and 2% as an emulsifier for paraffin oil. All the resulting emulsions are stable on storage.

EXAMPLE 22

300 parts of paraffin (solid), 15 parts of lactic acid and 15 parts of the reaction product according to Example 8 are stirred with 500 parts of water at 90 to 95° C. The mixture is then homogenised, whilst circulating, in a high pressure emulsifying pump, prewarmed to 90° C, for 5 minutes under a pressure of 300 bars. A colloidal, pourable emulsion is obtained which is suitable for providing cotton and viscose fabrics with a water-repellent finish by the pad process.

EXAMPLE 23

The emulsion which follows is prepared with the reaction product according to Example 6 as the emulsifier:

0.5 g of the product from Example 6,
25 g of stearyl 2,3-dihydroxypropyl ether and
120 g of distilled water.

The mixture is warmed to 80° C, whilst stirring, and homogenised for 120 seconds. The emulsion thus obtained is stable and can be diluted with water in any desired proportions. It gives a good anti-static finish to synthetic fibres.

EXAMPLE 24

1%, 5% or 10% of a solid disperse dyestuff (fineness of grinding 5 to 15μ, free from dispersing agent) are added to the emulsion B according to Example 17 and the mixtures are homogenised. All three emulsions are stable even at the boiling point and do not foam.

EXAMPLE 25

0.5 part of the reaction product from Example 4 is suspended in 24.5 parts of deionised water. Thereafter, 75 parts of paraffin oil are emulsified into the suspension in an emulsifying apparatus until a homogeneous stable emulsion is formed. Groundnut oil, castor oil, isopropyl myristate, octyl-dodecanol and corresponding combinations can also be used instead of paraffin oil.

The emulsions or creams can be used for skin care.

EXAMPLE 26

The following are melted together at 65° C to prepare the oil phase:
1.5 parts of cetyl alcohol,
7.0 parts of glycerol monostearate and
2.0 parts of paraffin oil The following are dissolved to prepare the aqueous phase:
1.0 part of the reaction product from Example 4 and
5.0 parts of glycerol in
83.0 parts of deionised water.

Thereafter, 0.5 part of methylcellulose is swollen in the aqueous phase at 65° C and the pH value is adjusted to 6 with lactic acid. The oil phase and the aqueous phase are emulsified together in a mixing apparatus and the emulsion is cooled to room temperature, whilst stirring.

A stable, supple cream which is easy to spread over the skin and which is also stable towards microbial decomposition is obtained.

EXAMPLE 27

1 part of the reaction product from Example 4 is dissolved in 39 parts of ethanol and the solution is filled into an aerosol packaging with 60 parts of propellant gas. This spray, applied to hair, causes a light setting and softening of the hair. The hair is supple and can be easily combed without dandruff forming and without flying away. The hair is shiny in appearance and the handle is pleasantly silky.

EXAMPLE 28

1 part of the reaction product from Example 4 is dissolved in 9 parts of alcohol and 90 parts of deionised water. This agent is applied to hair, water-waving is carried out, a good ease of combing when wet being achieved, and the hair is dried. The hair is set well and is supple and has an attractive shine. Long hair can also be combed easily and does not fly away. No dandruff forms and the product can be washed out again easily.

This hair setting lotion can also be used as a hair conditioning agent. Good care properties are thereby achieved.

EXAMPLE 29

An optical brightener of the formula

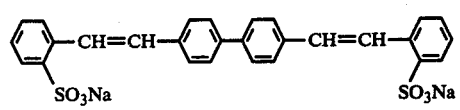

is triturated and mixed together with 5 ml of water in a mortar, prewarmed to 40° C. Thereafter, 10 to 20 ml of distilled water are added and a reaction product according to Example 4 is subsequently added, in a concentrated aqueous solution, as a stabiliser. The detergent (25 g) is then added and the constituents are mixed until a homogeneous paste is obtained.

The paste is first dried for 2 hours at 80° C and under 400 to 500 mm Hg and, after breaking up, is dried for a further 4 hours at 80° C and under 200 to 300 mm Hg.

The resulting powder is pressed through a sieve with a mesh width of 0.8 mm onto a sieve lying below with a mesh width of 0.315 mm. A powder of uniform particle size remains on the latter.

The powder prepared in this manner is stored in a climatically conditioned room at 20° C and 65% relative atmospheric humidity.

Without a stabiliser, depending on the concentration of the brightener (0.6 to 0.2% relative to the detergent), discolorations appear after a few hours, but at the latest after 16 hours. A stabiliser is considered to be effective when after at least 40 hours still no discoloration has appeared. In the present case, the concentration of the reaction product according to Example 4 necessary for stabilising is 3%, relative to the detergent.

The test detergent has the following composition:
15.7% of alkylarylsulphonate,
3.7% of fatty alcohol-sulphate,
2.7% of coconut acid monoethanolamide,
39.0% of Na tripolyphosphate,
4% of Na silicate,
2% of magnesium silicate,
1% of carboxymethylcellulose,
0.5% of Na ethylenediaminetetraacetate,
6.7% of water and
remainder to 100% = sodium sulphate.

We claim:

1. A boric acid/amine reaction product of (a) boric acid and (b) an amine of the formula

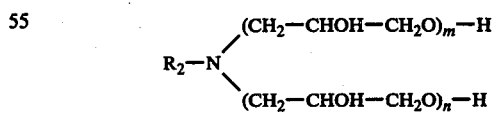

in which $R_2$ is alkyl with 1 to 22 carbon atoms, phenyl, alkylphenyl with 1 to 22 carbon atoms in the alkyl radical, cyclohexyl or a heterocyclic radical with 6 ring members and 1 or 2 nitrogen or oxygen atoms as heteroatoms and m and n each denote a number from 1 to 6.

2. A boric acid/amine reaction product according to claim 1, which has been obtained from (b) an amine of the formula

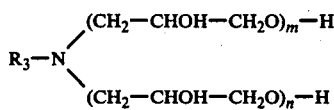

in which R₃ is alkyl with 1 to 22 carbon atoms.

3. A boric acid/amine reaction product according to claim 1, which has been obtained from an amine in which the indices m and n are each 1 or 2.

4. A boric acid/amine reaction product according to claim 1, which has been obtained from 1 mol of boric acid and 1 mol of amine.

5. A boric acid/amine reaction product according to claim 1, which corresponds to the formula

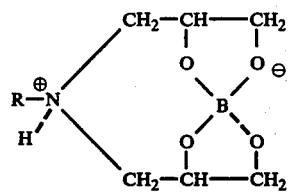

or contains structural elements of the formula

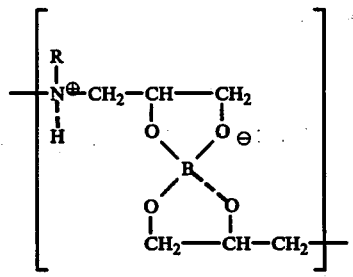

in which R has the meaning indicated in claim 1.

6. A boric acid/amine reaction product according to claim 1, which corresponds to the formula

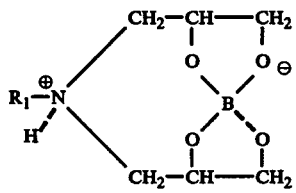

or contains structural elements of the formula

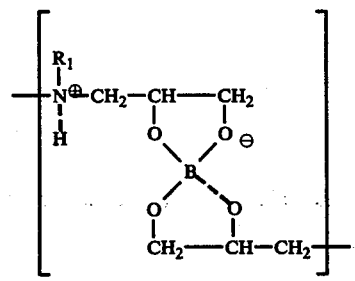

in which R₁ has the meaning indicated in claim 2.

7. A boric acid/amine reaction product according to claim 1, which corresponds to the formula

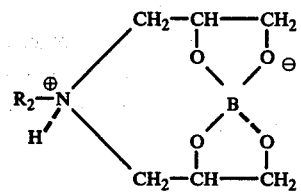

or contains structural elements of the formula

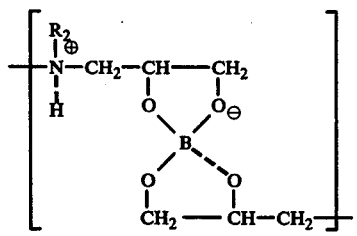

in which R₂ has the meaning indicated in claim 1.

8. A boric acid/amine reaction product according to claim 2, which corresponds to the formula

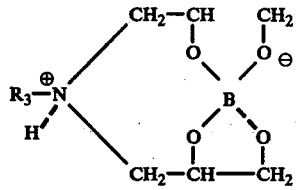

or contains structural elements of the formula

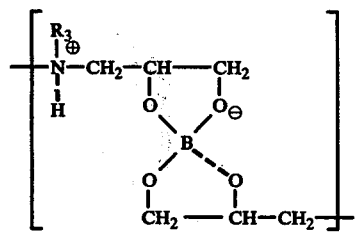

in which R₃ has the meaning indicated in claim 2.

9. A boric acid/amine reaction product according to claim 1, which is present in the form of a quaternization product or an amine oxide.

10. A process for the manufacture of a boric acid/amine reaction product of the composition indicated in claim 1, which comprises reacting (a) boric acid with (b) an amine of the formula

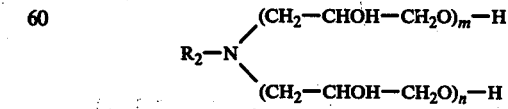

in which R₂ is alkyl with 1 to 22 carbon atoms, phenyl, alkylphenyl with 1 to 22 carbon atoms in the alkyl radical, cyclohexyl or a heterocyclic radical with 6 ring members and 1 or 2 nitrogen or oxygen atoms as heteroatoms and m and n each denote a number from 1 to 6, in the presence of an inert, organic solvent and optionally in the presence of a catalyst.

11. A process for the preparation of an aqueous emulsion or dispersion of a water-insoluble product, wherein this product is emulsified or dispersed in water in the presence of a boric acid/amine reaction product of the composition indicated in claim 1.

12. An aqueous formulation, in particular an emulsion or dispersion, for providing a textile material with a water-repellent or anti-static finish or a finish imparting a soft handle, which contains a boric acid/amine reaction product according to claim 1.

* * * * *